US008816305B2

(12) United States Patent
De Dea et al.

(10) Patent No.: US 8,816,305 B2
(45) Date of Patent: Aug. 26, 2014

(54) FILTER FOR MATERIAL SUPPLY APPARATUS

(75) Inventors: Silvia De Dea, San Diego, CA (US); Sergei Kalynych, San Diego, CA (US); Peter Baumgart, San Diego, CA (US)

(73) Assignee: ASML Netherlands B.V., Veldhoven (NL)

( * ) Notice: Subject to any disclaimer, the term of this patent is extended or adjusted under 35 U.S.C. 154(b) by 256 days.

(21) Appl. No.: 13/330,884

(22) Filed: Dec. 20, 2011

(65) Prior Publication Data

US 2013/0153603 A1 Jun. 20, 2013

(51) Int. Cl.
*A61N 5/06* (2006.01)
*A61N 5/00* (2006.01)
*G21G 4/00* (2006.01)

(52) U.S. Cl.
USPC ................. 250/504 R; 250/492.2; 250/493.1; 378/119

(58) Field of Classification Search
USPC .................... 222/189.06, 146.2, 325; 239/86; 210/510.1, 500.1, 348; 250/492.1, 250/492.2, 493.1, 504 R; 347/35, 37; 378/119
See application file for complete search history.

(56) References Cited

U.S. PATENT DOCUMENTS

| | | | | |
|---|---|---|---|---|
| 1,261,495 | A * | 4/1918 | Doolin | 222/189.06 |
| 2,807,288 | A * | 9/1957 | Shea | 141/18 |
| 3,285,296 | A * | 11/1966 | Ishimaru et al. | 73/864.02 |
| 3,955,953 | A | 5/1976 | Hauser | |
| 5,662,271 | A | 9/1997 | Weston et al. | |
| 6,315,168 | B1 * | 11/2001 | Bolyard et al. | 222/189.06 |
| 6,835,944 | B2 | 12/2004 | Orsini et al. | |
| 7,122,816 | B2 | 10/2006 | Algots et al. | |
| 7,128,772 | B2 | 10/2006 | Brueck | |
| 7,405,416 | B2 | 7/2008 | Algots et al. | |
| 7,449,703 | B2 | 11/2008 | Bykanov | |
| 7,465,946 | B2 | 12/2008 | Bowering et al. | |
| 7,872,245 | B2 | 1/2011 | Vaschenko et al. | |
| 8,182,127 | B2 * | 5/2012 | Yasuda et al. | 362/553 |
| 8,198,615 | B2 * | 6/2012 | Bykanov et al. | 250/504 R |
| 8,462,425 | B2 * | 6/2013 | Hou et al. | 359/333 |
| 8,497,489 | B2 * | 7/2013 | Yabu et al. | 250/504 R |
| 8,513,629 | B2 * | 8/2013 | Rajyaguru et al. | 250/504 R |
| 2006/0134397 | A1 | 6/2006 | Smith | |
| 2006/0192155 | A1 | 8/2006 | Algots et al. | |
| 2007/0215723 | A1 | 9/2007 | Moser et al. | |
| 2007/0252877 | A1 | 11/2007 | Okubo | |
| 2007/0267353 | A1 | 11/2007 | Mak et al. | |

OTHER PUBLICATIONS

International Search Report of the International Searching Authority, issued on Jan. 29, 2013, 2 pages, in counterpart application PCT/US12/66122.

Written Opinion of the International Searching Authority, issued on Jan. 29, 2013, 6 pages, in counterpart application PCT/US12/66122.

* cited by examiner

*Primary Examiner* — Kevin P Shaver
*Assistant Examiner* — Stephanie E Williams
(74) *Attorney, Agent, or Firm* — DiBerardino McGovern IP Group LLC

(57) ABSTRACT

An apparatus supplies a target material to a target location. The apparatus includes a reservoir that holds a target mixture that includes the target material and non-target particles; a supply system that receives the target mixture from the reservoir and that supplies the target mixture to the target location, the supply system including a tube and a nozzle that defines an orifice through which the target mixture is passed; and a filter inside the tube through which the target mixture is passed.

23 Claims, 8 Drawing Sheets

FILTER FOR MATERIAL SUPPLY APPARATUS

TECHNICAL FIELD

The disclosed subject matter relates to a filter for use in a target material supply apparatus.

BACKGROUND

Extreme ultraviolet ("EUV") light, for example, electromagnetic radiation having wavelengths of around 50 nm or less (also sometimes referred to as soft x-rays), and including light at a wavelength of about 13 nm, can be used in photolithography processes to produce extremely small features in substrates, for example, silicon wafers.

Methods to produce EUV light include, but are not necessarily limited to, converting a material into a plasma state that has an element, for example, xenon, lithium, or tin, with an emission line in the EUV range. In one such method, often termed laser produced plasma ("LPP"), the required plasma can be produced by irradiating a target material, for example, in the form of a droplet, stream, or cluster of material, with an amplified light beam that can be referred to as a drive laser. For this process, the plasma is typically produced in a sealed vessel, for example, a vacuum chamber, and monitored using various types of metrology equipment.

SUMMARY

In one general aspect, an apparatus supplies a target material to a target location. The apparatus includes a reservoir that holds a target mixture that includes the target material and non-target particles; a supply system that receives the target mixture from the reservoir and that supplies the target mixture to the target location, the supply system including a tube and a nozzle that defines an orifice through which the target mixture is passed; and a filter inside the tube through which the target mixture is passed.

Implementations can include one or more of the following features. For example, the filter can be a sintered filter.

The filter and the tube can be arranged so that the target mixture passes through the filter. The filter can include pores through which the target material passes. The size of the pores within the filter can be determined by the size of the nozzle and orifice. The size of the nozzle and the orifice can be determined by the size of the target material.

The filter pores can be uniformly sized or non-uniformly sized. The tube can be a capillary tube.

The apparatus can include another filter that is upstream of the supply system. The filter can have a coarser porous structure than the other filter. The filter can have a finer porous structure than the other filter. The other filter can be a sintered filter.

One or more of the filter, the tube, and the nozzle can be made of glass. The glass can be fused silica or fused quartz.

The filter can be integrated with the tube. The filter can be bonded to the internal wall of the tube. The filter can be placed within the tube adjacent the nozzle.

The filter can be a porous fitted filter. The filter can be made of a material that does not chemically react with the target mixture. The filter can be made of ceramic.

In another general aspect, a target material is supplied to a target location using a method. The method includes heating a bulk substance of a target mixture until the bulk substance becomes a fluid of the target mixture, the target mixture including target material and non-target particles; holding the target mixture fluid within a reservoir; passing the target mixture fluid through a nozzle tube of a supply system; filtering at least some of the non-target particles from the target mixture fluid as the target mixture fluid passes through the supply system nozzle tube; and supplying the filtered target mixture fluid to the target location including passing the filtered target mixture through an orifice of a nozzle defined at the end of the nozzle tube.

In another general aspect, an apparatus is configured to supply a target material to a target location. The apparatus includes a supply system that is configured to receive a target mixture from a reservoir and to supply the target mixture to a target location. The supply system includes a capillary tube defining an internal passageway and a nozzle at an end of the capillary tube. The nozzle defines an orifice. The apparatus also includes a filter inside of the internal passageway of the capillary tube and integrated with the capillary tube such that the target mixture would need to pass through pores within the filter while traveling through the capillary tube.

DRAWING DESCRIPTION

DESCRIPTION

This description relates to the use of a filter and a method of filtering within a hollow tube of a supply system of a target material delivery system for removing the impurities (such as non-target particles) within a target mixture. The supply system is at the output of a reservoir that stores the target mixture such that the supply system receives the target mixture and supplies the target mixture in the form of droplets to a target location for an LPP EUV light source. A description of the components of an LPP EUV light source will initially be described as background before a detailed description of the target material delivery system.

Figure 1:
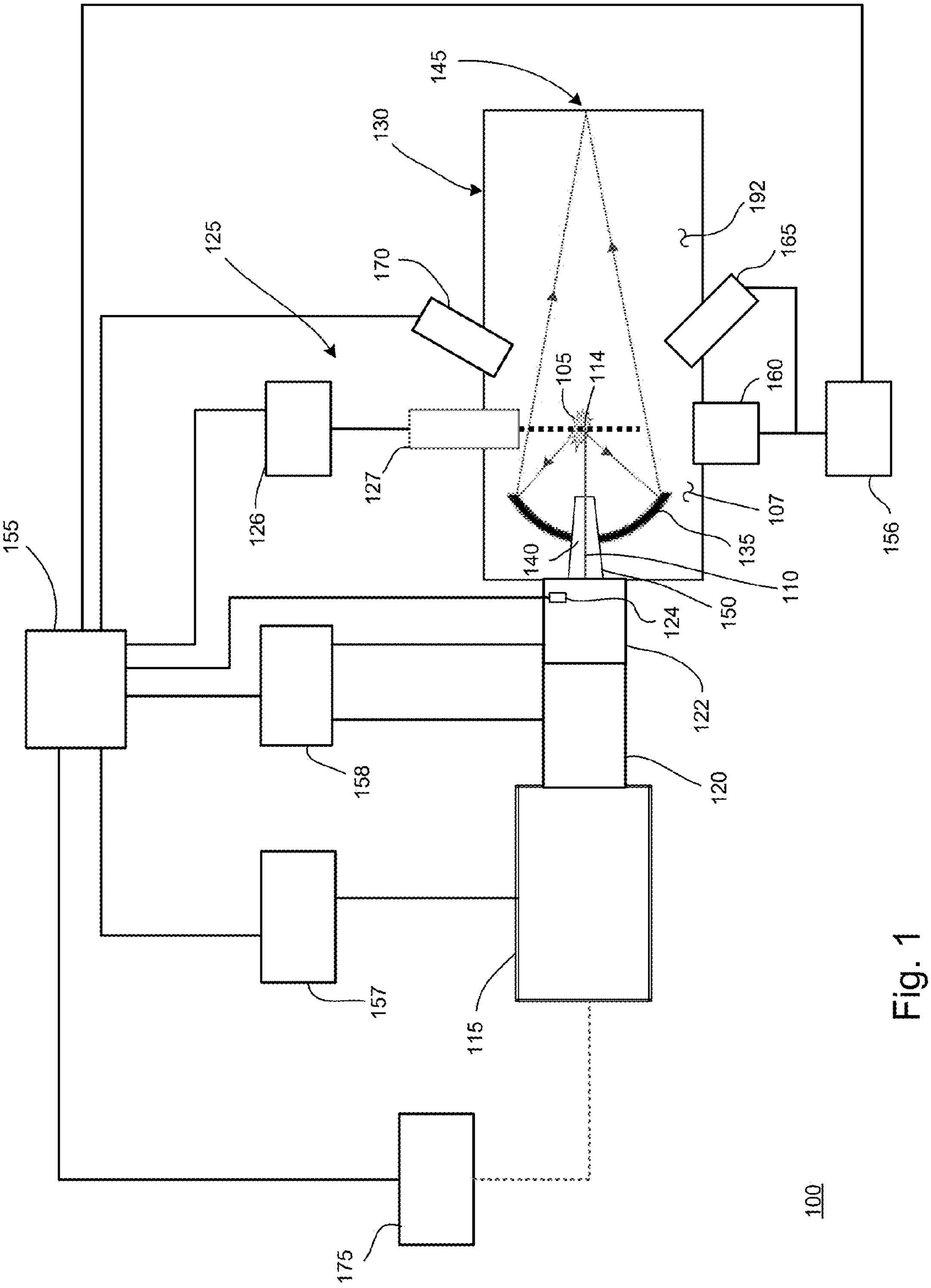
FIG. 1 is a block diagram of a laser produced plasma (LPP) extreme ultraviolet (EUV) light source.

Referring to FIG. 1, an LPP EUV light source 100 is formed by irradiating a target mixture 114 at a target location 105 with an amplified light beam 110 that travels along a beam path toward the target mixture 114. The target location 105, which is also referred to as the irradiation site, is within an interior 107 of a vacuum chamber 130. When the amplified light beam 110 strikes the target mixture 114, a target material within the target mixture 114 is converted into a plasma state that has an element with an emission line in the EUV range. The created plasma has certain characteristics that depend on the composition of the target material within the target mixture 114. These characteristics can include the wavelength of the EUV light produced by the plasma and the type and amount of debris released from the plasma.

The light source 100 also includes a target material delivery system 125 that delivers, controls, and directs the target mixture 114 in the form of liquid droplets, a liquid stream, solid particles or clusters, solid particles contained within liquid droplets or solid particles contained within a liquid stream. The target mixture 114 includes the target material such as, for example, water, tin, lithium, xenon, or any material that, when converted to a plasma state, has an emission line in the EUV range. For example, the element tin can be used as pure tin (Sn); as a tin compound, for example, $SnBr_4$, $SnBr_2$, $SnH_4$; as a tin alloy, for example, tin-gallium alloys, tin-indium alloys, tin-indium-gallium alloys, or any combination of these alloys. The target mixture 114 can also include impurities such as non-target particles. Thus, in the situation in which there are no impurities, the target mixture 114 is made up of only the target material. The target mixture 114 is delivered by the target material delivery system 125 into the interior 107 of the chamber 130 and to the target location 105.

The light source 100 includes a drive laser system 115 that produces the amplified light beam 110 due to a population inversion within the gain medium or mediums of the laser system 115. The light source 100 includes a beam delivery system between the laser system 115 and the target location 105, the beam delivery system including a beam transport system 120 and a focus assembly 122. The beam transport system 120 receives the amplified light beam 110 from the laser system 115, and steers and modifies the amplified light beam 110 as needed and outputs the amplified light beam 110 to the focus assembly 122. The focus assembly 122 receives the amplified light beam 110 and focuses the beam 110 to the target location 105.

In some implementations, the laser system 115 can include one or more optical amplifiers, lasers, and/or lamps for providing one or more main pulses and, in some cases, one or more pre-pulses. Each optical amplifier includes a gain medium capable of optically amplifying the desired wavelength at a high gain, an excitation source, and internal optics. The optical amplifier may or may not have laser mirrors or other feedback devices that form a laser cavity. Thus, the laser system 115 produces an amplified light beam 110 due to the population inversion in the gain media of the laser amplifiers even if there is no laser cavity. Moreover, the laser system 115 can produce an amplified light beam 110 that is a coherent laser beam if there is a laser cavity to provide enough feedback to the laser system 115. The term “amplified light beam” encompasses one or more of: light from the laser system 115 that is merely amplified but not necessarily a coherent laser oscillation and light from the laser system 115 that is amplified and is also a coherent laser oscillation.

The optical amplifiers in the laser system 115 can include as a gain medium a filling gas that includes $CO_2$ and can amplify light at a wavelength of between about 9100 and about 11000 nm, and in particular, at about 10600 nm, at a gain greater than or equal to 1000. Suitable amplifiers and lasers for use in the laser system 115 can include a pulsed laser device, for example, a pulsed, gas-discharge $CO_2$ laser device producing radiation at about 9300 nm or about 10600 nm, for example, with DC or RF excitation, operating at relatively high power, for example, 10 kW or higher and high pulse repetition rate, for example, 50 kHz or more. The optical amplifiers in the laser system 115 can also include a cooling system such as water that can be used when operating the laser system 115 at higher powers.

The light source 100 includes a collector mirror 135 having an aperture 140 to allow the amplified light beam 110 to pass through and reach the target location 105. The collector mirror 135 can be, for example, an ellipsoidal mirror that has a primary focus at the target location 105 and a secondary focus at an intermediate location 145 (also called an intermediate focus) where the EUV light can be output from the light source 100 and can be input to, for example, an integrated circuit lithography tool (not shown). The light source 100 can also include an open-ended, hollow conical shroud 150 (for example, a gas cone) that tapers toward the target location 105 from the collector mirror 135 to reduce the amount of plasma-generated debris that enters the focus assembly 122 and/or the beam transport system 120 while allowing the amplified light beam 110 to reach the target location 105. For this purpose, a gas flow can be provided in the shroud that is directed toward the target location 105.

The light source 100 can also include a master controller 155 that is connected to a droplet position detection feedback system 156, a laser control system 157, and a beam control system 158. The light source 100 can include one or more target or droplet imagers 160 that provide an output indicative of the position of a droplet, for example, relative to the target location 105 and provide this output to the droplet position detection feedback system 156, which can, for example, compute a droplet position and trajectory from which a droplet position error can be computed either on a droplet by droplet basis or on average. The droplet position detection feedback system 156 thus provides the droplet position error as an input to the master controller 155. The master controller 155 can therefore provide a laser position, direction, and timing correction signal, for example, to the laser control system 157 that can be used, for example, to control the laser timing circuit and/or to the beam control system 158 to control an amplified light beam position and shaping of the beam transport system 120 to change the location and/or focal power of the beam focal spot within the chamber 130.

The target material delivery system 125 includes a target material delivery control system 126 that is operable in response to a signal from the master controller 155, for example, to modify the release point of the droplets as released by a target material supply apparatus 127 to correct for errors in the droplets arriving at the desired target location 105.

Additionally, the light source 100 can include a light source detector 165 that measures one or more EUV light parameters, including but not limited to, pulse energy, energy distribution as a function of wavelength, energy within a particular band of wavelengths, energy outside of a particular band of wavelengths, and angular distribution of EUV intensity and/or average power. The light source detector 165 generates a feedback signal for use by the master controller 155. The feedback signal can be, for example, indicative of the errors in parameters such as the timing and focus of the laser pulses to properly intercept the droplets in the right place and time for effective and efficient EUV light production.

The light source 100 can also include a guide laser 175 that can be used to align various sections of the light source 100 or to assist in steering the amplified light beam 110 to the target location 105. In connection with the guide laser 175, the light source 100 includes a metrology system 124 that is placed within the focus assembly 122 to sample a portion of light from the guide laser 175 and the amplified light beam 110. In other implementations, the metrology system 124 is placed within the beam transport system 120. The metrology system 124 can include an optical element that samples or re-directs a subset of the light, such optical element being made out of any material that can withstand the powers of the guide laser beam and the amplified light beam 110. A beam analysis system is formed from the metrology system 124 and the master controller 155 since the master controller 155 analyzes the sampled light from the guide laser 175 and uses this information to adjust components within the focus assembly 122 through the beam control system 158.

Thus, in summary, the light source 100 produces an amplified light beam 110 that is directed along the beam path to irradiate the target mixture 114 at the target location 105 to convert the target material within the mixture 114 into plasma that emits light in the EUV range. The amplified light beam 110 operates at a particular wavelength (that is also referred to as a source wavelength) that is determined based on the design and properties of the laser system 115. Additionally, the amplified light beam 110 can be a laser beam when the target material provides enough feedback back into the laser system 115 to produce coherent laser light or if the drive laser system 115 includes suitable optical feedback to form a laser cavity.

Figure 2:
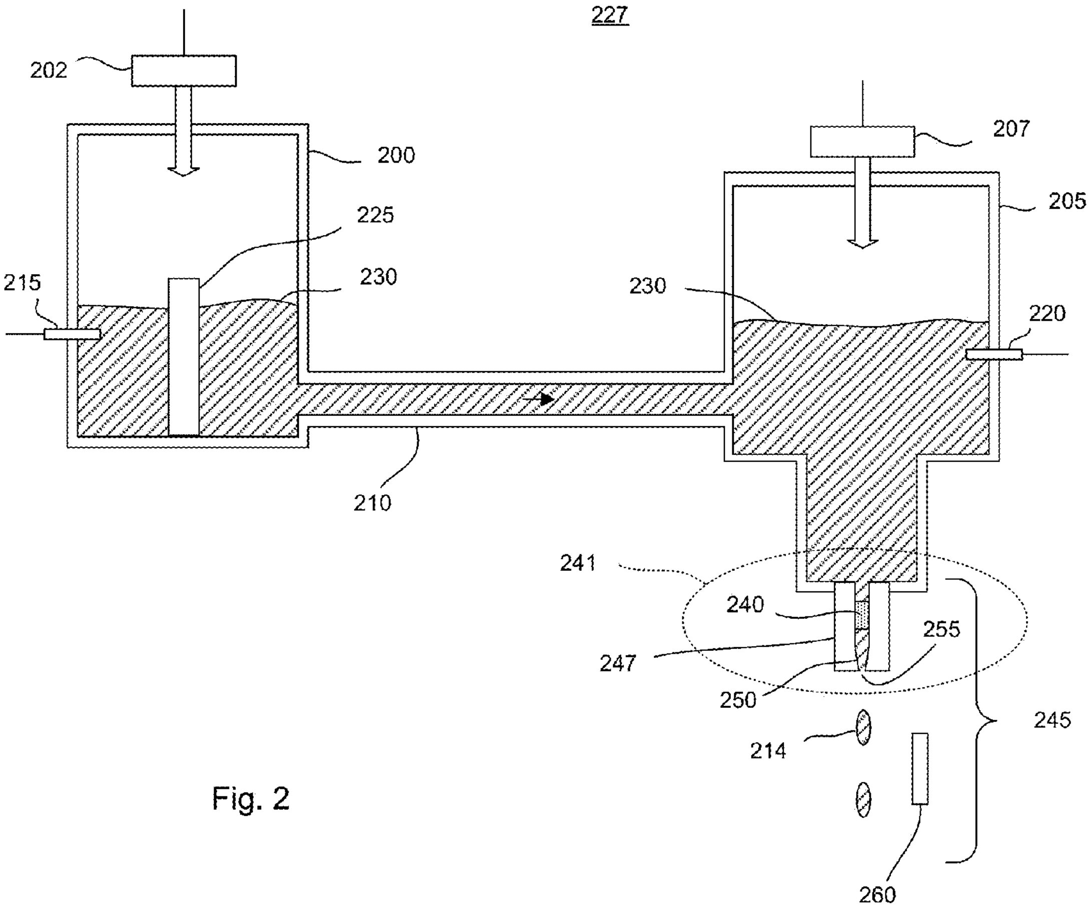
FIG. 2 is a schematic cross-sectional diagram of an exemplary target material supply apparatus of the light source of FIG. 1.

Referring to FIG. 2, in an exemplary implementation, a target material supply apparatus 227 includes two chambers, a first chamber 200 (which is also referred to as a bulk material chamber or reservoir) and a second chamber 205 (which is also referred to as a vessel) fluidly coupled to the first chamber 200 by a pipe 210 that can be fitted with a valve to control the flow of material between the first chamber 200 and the second chamber 205. The first and second chambers 200, 205 may be hermetically sealed volumes with independent, active pressure controllers 202, 207. The first and second chambers 200, 205, and the pipe 210 can be thermally coupled to one or more heaters that control the temperature of the first and second chambers 200, 205 and the pipe 210. Additionally, the apparatus 227 can also include one or more level sensors 215, 220 that detect an amount of substance within each of the respective chambers 200, 205. The output of the level sensors 215, 220 can be fed to the control system 126, which is also connected to the pressure controllers 202, 207.

The first chamber 200 includes a bulk substance 225, which becomes a fluid, which can be a liquid, a gas, or a plasma; the resultant fluid is referred to as a target mixture 230. The target mixture 230 includes the target material plus other non-target particles.

The apparatus 227 also includes a supply system 245 at the output of the second chamber 205. The supply system 245 receives the target mixture 230 that has passed through the chambers 200, 205 and supplies the target mixture in the form of droplets 214 to the target location 105. To this end, the supply system 245 can include a hollow tube 247 and a nozzle 250 defining an orifice 255 through which the target mixture 230 escapes to form the droplets 214 of the target mixture. The output of the droplets 214 can be controlled by an actuator such as a piezoelectric actuator. Additionally, the supply system 245 can include other regulating or directing components 260 downstream of the nozzle 250. The nozzle 250 and/or the directing components 260 direct the droplets 214 (which is the target mixture 230 that has been filtered to include the target material and a lot less of the impurities) to the target location 105.

The apparatus 227 includes one or more filters 240 that are placed in the path of the flow of the target mixture 230 from the bulk substance 225 to the orifice 255 of the supply system 245. At least one of these filters 240 is placed within the tube 247 of the supply system 245. The filter 240 removes impurities such as the non-target particles from the target mixture 230.

Figure 4:
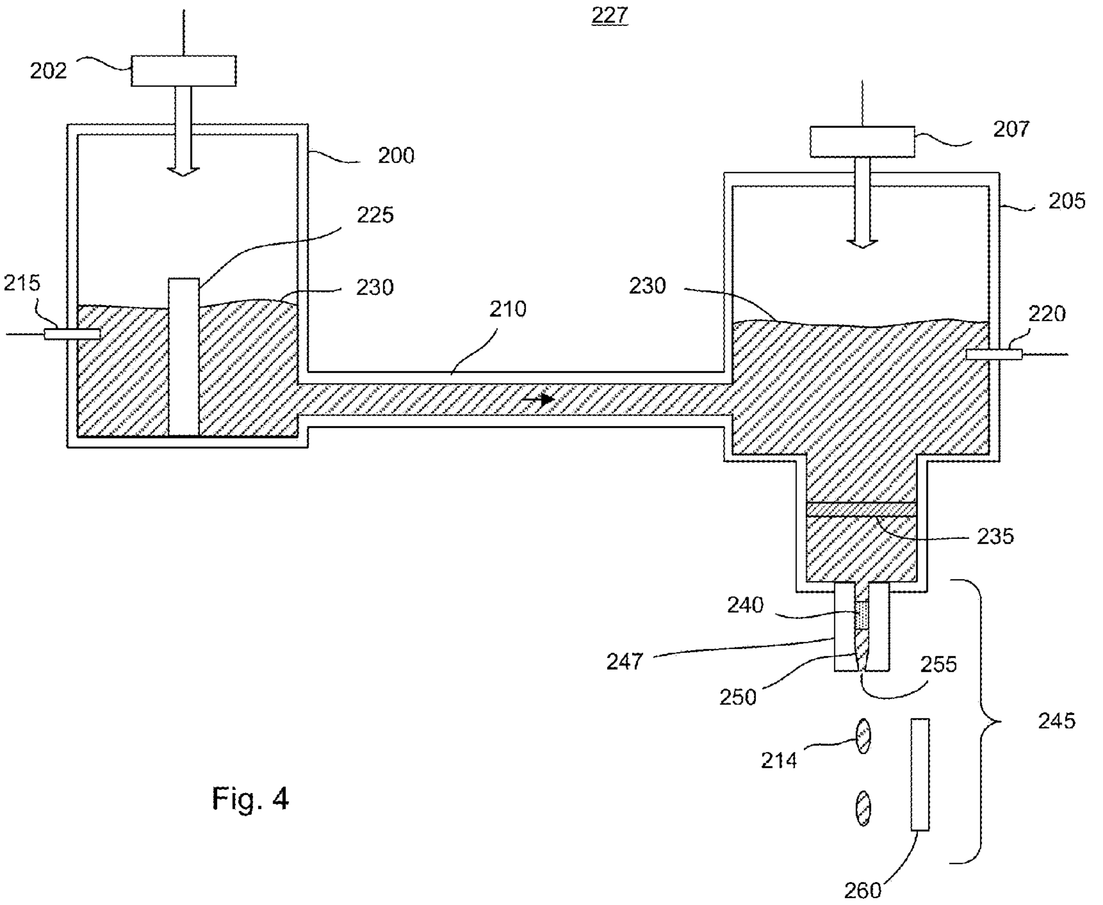
FIG. 4 is a schematic cross-sectional diagram of an exemplary target material supply apparatus of the light source of FIG. 1.

As shown in FIG. 2, the single filter 240 can be used as the primary filter in the apparatus 227 if the level of contamination of non-target particles within the chambers 200, 205 is substantially low enough that another filter upstream of the filter 240 (for example, within one of the chambers 200, 205 as shown in FIG. 4) is not needed.

Figure 3A:
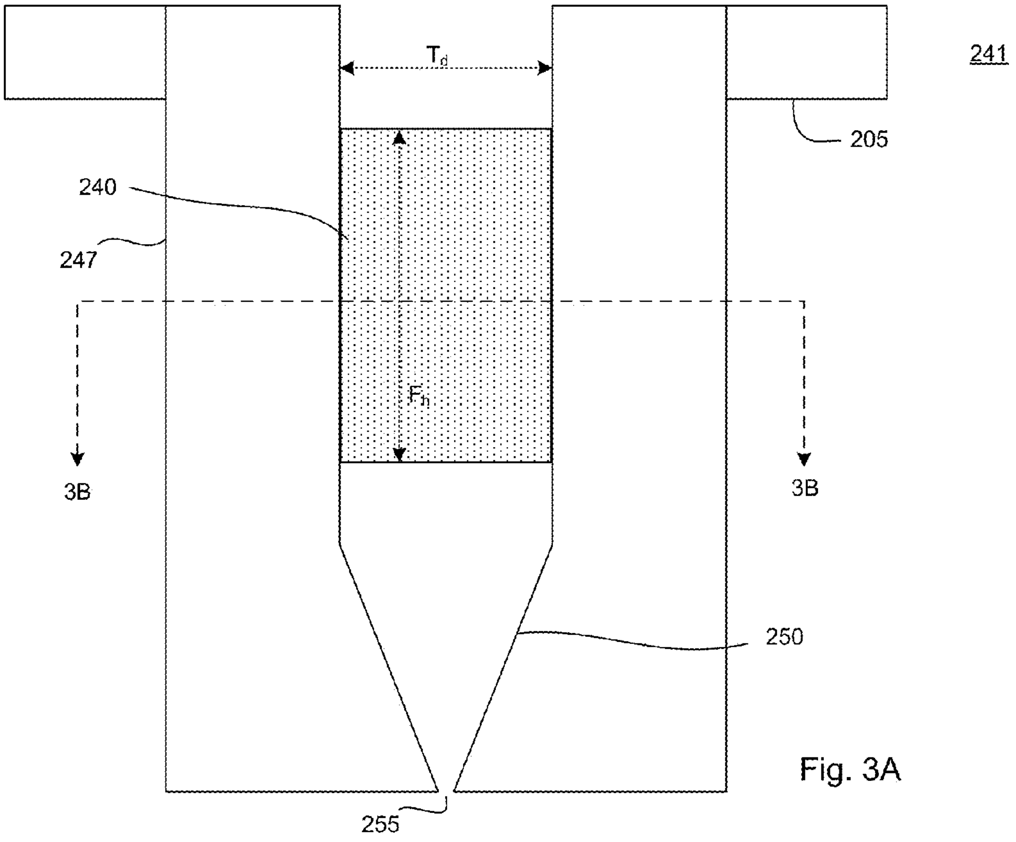
FIG. 3A is a schematic cross-sectional diagram of an exemplary supply system of the apparatus of FIG. 2.
Figure 3B:
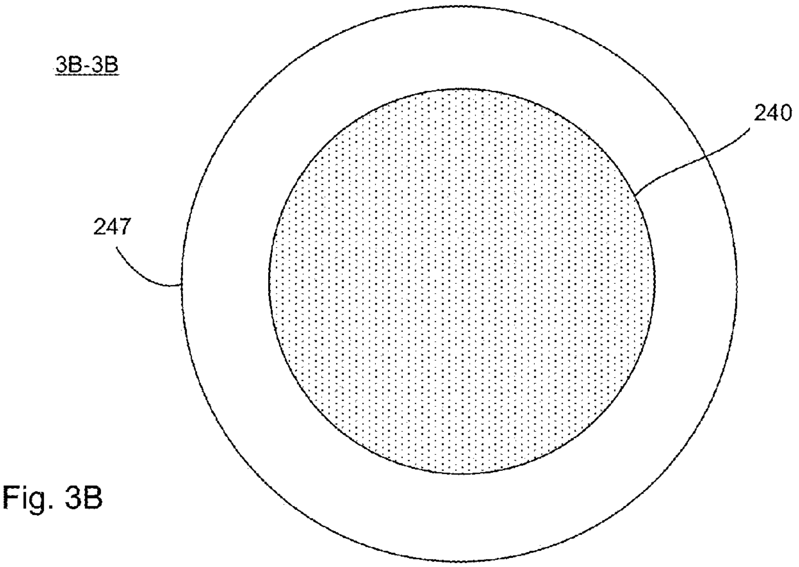
FIG. 3B is a diagram of an exemplary tube of the supply system of FIG. 3A taken along section 3B-3B.

Referring also to FIGS. 3A and 3B, the filter 240 is integrated with the tube 247 such that the target mixture 230 passes or flows through pores within the filter 240 as it moves through the tube 247 toward the nozzle 250. The target mixture 230 is substantially prevented from flowing around the edges of the filter 240 or between the filter 240 and the interior surface of the tube 247. In particular, the filter 240 is integrated with the interior surface of the tube 247 such that the filter 240 is bonded to or adhered to the interior surface of the tube 247.

There are different ways to accomplish this integration. One way is to insert a pre-made filter into the tube 247 and then bond or adhere the filter to the interior surface of the tube 247 using a bonding agent (such as glue) or using thermal technique that heats the materials to bond them together. The material of the filter 240 should be compatible with the bonding agent and the surface of the tube 247.

The pre-made filter 240 can be a sintered filter or a mesh filter. In this case, the filter includes pores or holes that may be non-uniform in cross-sectional size such that the holes can range in size along a distribution between a lower size and an upper size. The cross-sectional size is the size of the pore taken along the plane that is perpendicular to the general direction of flow of the fluid through the filter. Moreover, the distribution of cross-sectional sizes need not be symmetric about the average pore size. For example, in one implementation, if the average cross-sectional size of a pore of the filter 240 is about 0.2 μm, the pore size distribution can range from about 0.1 μm to about 1.0 μm.

Alternatively, the pre-made filter 240 can be a filter that is a non-sintered, non-mesh filter that includes at least a set of uniformly-sized through holes formed between opposing flat surfaces. In this case, the filter through holes are formed into a bulk substance and extend from a flat surface facing the second chamber 205 to a flat surface facing the nozzle 250 so that the holes are fluidly coupled at a first end to the second chamber 205 that holds the target mixture 230, and are fluidly coupled at a second end to the orifice 255 of the nozzle 250. In some implementations, all of the holes of the filter 240 can be through holes such that the target material is able to pass entirely through every one of the holes of the filter 240 while the holes are small enough to block the non-target particles.

Another way to accomplish integration between the filter 240 and the interior surface of the tube 247 is to insert a pre-cursor material into the tube 247, and then process the pre-cursor material and the tube 247 together to form a porous filter 240 integrated with the tube 247. For example, the tube 247 can be made of glass (which includes substances such as quartz or silica) and can be a capillary tube, which has thick walls relative to the size of its inner bore. The pre-cursor material for the filter 240 can be glass beads that are inserted into the bore of the capillary tube, then heated with the capillary tube 247 to form a sintered glass filter integrated with the capillary tube 247. In this implementation, the pores of the filter 240 have a cross-sectional size that is distributed about an average pore size and the pore sizes are non-uniform.

In one particular example, the inner diameter of the tube 247 is about 200-500 μm, the outer diameter of the filter 240 is the same as the inner diameter of the tube 247 (because they are integrated with each other), the height $F_h$ (the distance taken along the general flow path of the target material 230) of the filter 240 is about 1-3 mm, and the overall length of the tube 247 is about 1-4 cm. The size of the pores within the filter 240 depend at least in part on the target mixture 230 and the size of both the non-target particles and the target material, the size of the orifice 255 and tube 247, and the flow rate of the target material 230. For a target material that is tin, pores in the filter 240 can have exemplary cross-sectional sizes of about 0.1-0.5 μm.

Referring also to FIG. 4, in another implementation, the target material supply apparatus 227 includes a second filter 235 upstream of the filter 240. The second filter 235 can be within any one of the first chamber 200, the pipe 210, or the second chamber 205. In this example, the second filter 235 is within the second chamber 205.

The second filter 235 can be a sintered filter or a mesh filter. In other implementations, the second filter 235 can be designed by machining or etching a bulk substance to form at least a set of uniformly-sized through holes, as described in U.S. application Ser. No. 13/112,784, filed on May 20, 2011, which is incorporated herein by reference in its entirety.

In general, the filter 240 can be made from a first material and the second filter 235 can be made of a second material that is distinct from the first material. In this way, if the second material does not adequately remove the non-target particles from the target mixture 230 or if target material causes the second material to leach from the second filter 235 into the target mixture 230, then the first material can be selected to be distinct from the second material to provide for the benefits not adequately provided for by the second material. Thus, the first material can be selected to remove the leached second material from the target mixture 230 or to more adequately remove other non-target particles from the target mixture 230. For example, if the second material is titanium, then the first material can be tungsten or glass.

Moreover, the holes of the filter 240 can have a cross-sectional width that is different from a cross-sectional width of the holes of the second filter 235. Thus, in one implementation, the holes or pores of the filter 240 have a cross-sectional width that is less than the cross-sectional width of the holes or pores of the second filter 235. In this way, the filter 240 would be designed to remove smaller non-target particles in the target mixture 230 than the second filter 235. In other implementations, the holes or pores of the filter 240 have a cross-sectional width that is equal to or greater than a cross-sectional width of the holes or pores of the second filter 235. In this way, the filter 240 can be designed to remove non-target particles that were introduced into the target mixture 230 by the second filter 235.

Figure 5:
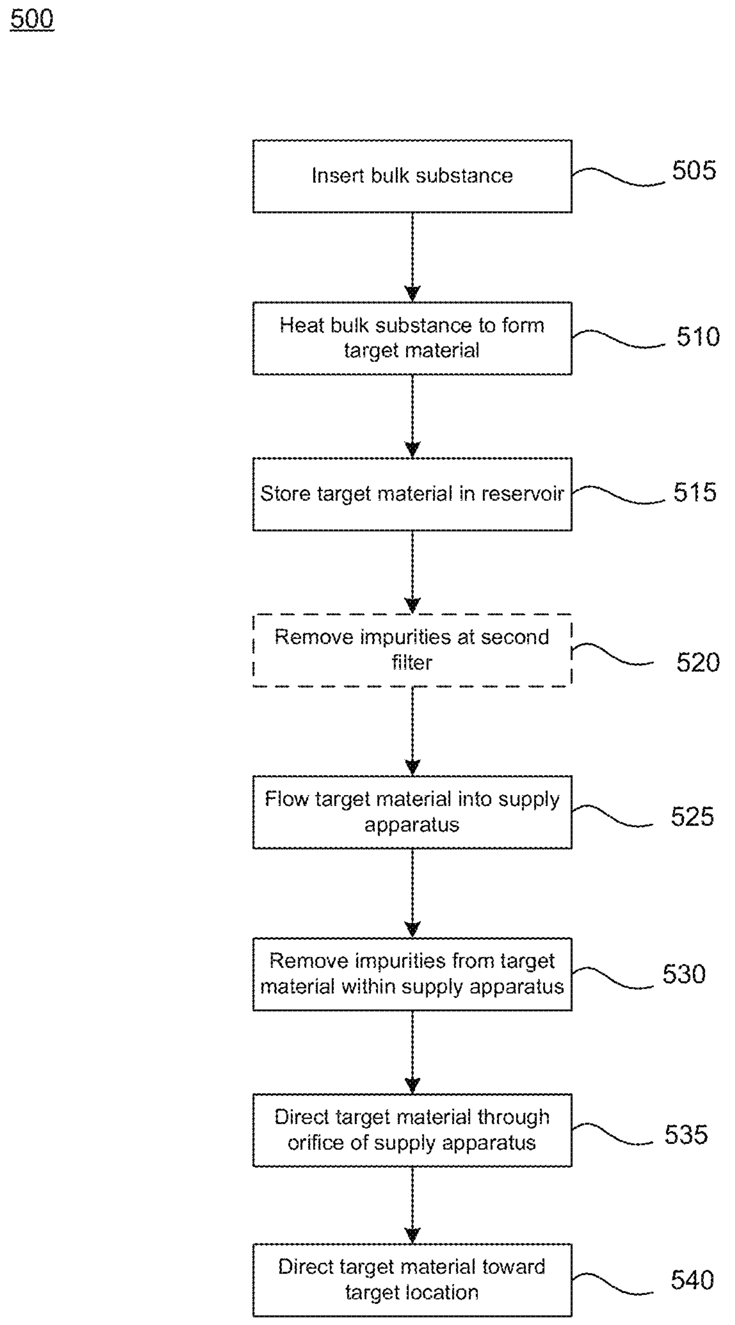
FIG. 5 is a procedure performed during operation of the target material supply apparatus of FIGS. 2 and 4.

Referring to FIG. 5, the target material supply apparatus 127 operates according to a procedure 500, as follows. An operator fills the first chamber 200 with a bulk substance 225 (step 505), and heats up the substance 225 using the heater thermally coupled to the first chamber 200 until the bulk substance 225 becomes a fluid (step 510). The resultant fluid can be a liquid, a gas, or a plasma and it can be referred to as the target mixture 230 that includes the target material plus the other non-target particles. At step 510, the pipe 210 and the second chamber 205 may also be heated by their respective heaters to maintain the target mixture 230 as a fluid throughout the supply apparatus 127.

The control system 126 receives inputs from the level sensors 215, 220, and controls the heaters to melt a given amount of the substance 225. The control system 126 also controls the pressure in each of the chambers 200, 205 and the opening and closing of the valve in the pipe 210. A description of an exemplary arrangement of the first and second chambers 200, 205 is found in U.S. Pat. No. 7,122,816, which is incorporated herein by reference in its entirety.

The target mixture 230 flows through the pipe 210, and into the second chamber 205, where it is stored for use by the supply system 245 (step 515). If the supply apparatus 227 includes the second filter 235 within the second chamber 205 (as shown in FIG. 4), then at least some of the impurities (that is, the non-target particles) in the target mixture 230 are removed within the second chamber 205 by the second filter 235 (step 520).

The target mixture 230 flows into the tube 247 (step 525), where non-target particles, which can include material produced at the second filter 235 if a second filter 235 is included within the supply apparatus 227, are blocked or removed by the filter 240 (step 530).

The target mixture 230 exits the filter 240 with fewer non-target particles than were present in the target mixture 230 that entered the filter 240. The target mixture 230 exiting the filter 240 escapes through the orifice 255 in the form of droplets 214 (step 535). The rate at which the droplets 214 are output and the size and shape of the droplets 214 can be controlled at least in part by an actuator such as a piezoelectric actuator or by the size and shape of the orifice 255. The nozzle 250 and the directing components 260 direct the droplets 214 to the target location 105 (step 540).

The filter 240 placed within the tube 247 reduces the accumulation of non-target particles within the orifice 255, such non-target particles can cause instability in the droplets or a loss of flow of the droplets output from the orifice 255. Moreover, when the filter 240 is used downstream of a second filter 235, the filter 240 is provided to reduce the number of non-target particles that pass through the filter 235 from reaching the orifice 255. Because the filter 240 is made of a material that does not chemically react with the target mixture 230, fewer additional non-target particles are produced at the filter 240 to further reduce clogging at the orifice 255.

Figure 6A:
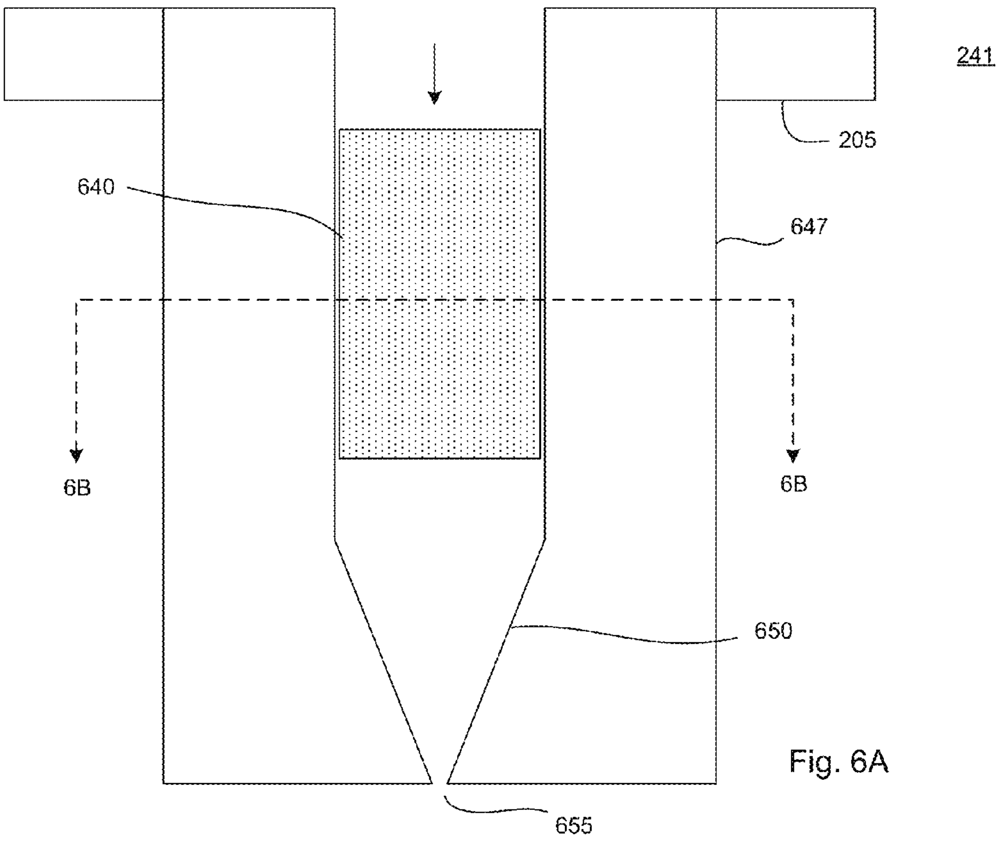
FIG. 6A is a schematic cross-sectional diagram of an exemplary supply system of the apparatus of FIG. 2.
Figure 6B:
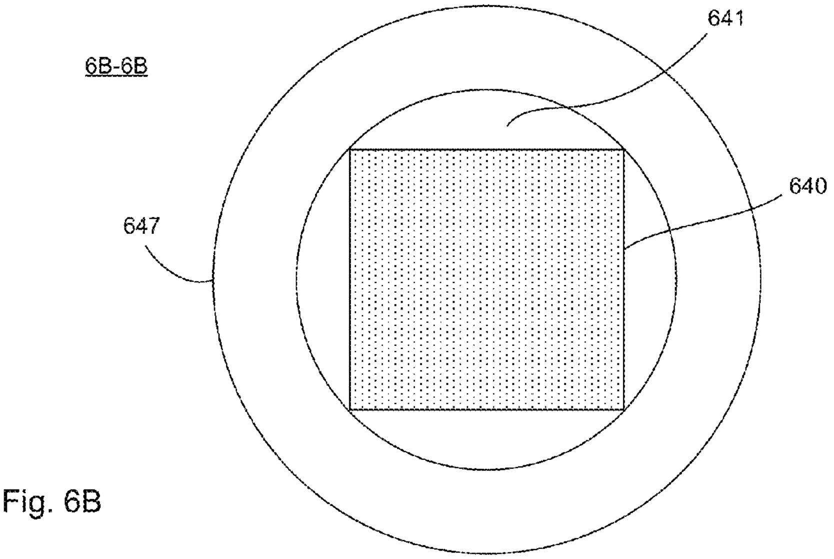
FIG. 6B is a diagram of an exemplary tube of the supply system of FIG. 6A taken along section 6B-6B.

Referring also to FIGS. 6A and 6B, in another implementation, the filter 640 is a solid material and is not integrated with the tube 647. In this implementation, the filter 640 is inserted inside the tube 647, and is geometrically configured to permit the target material of the target mixture 630 to pass through a space 641 between the filter 640 and the tube 647 so that the non-target particles are too large to fit through the space 641 between the filter 640 and the tube 647. In this example, the filter 640 has a rectangular cross-sectional geometry so that the space 641 through which the target material passes is the space between the planar outer surface of the filter 640 and the inner circular surface of the tube 647.

Figure 7:
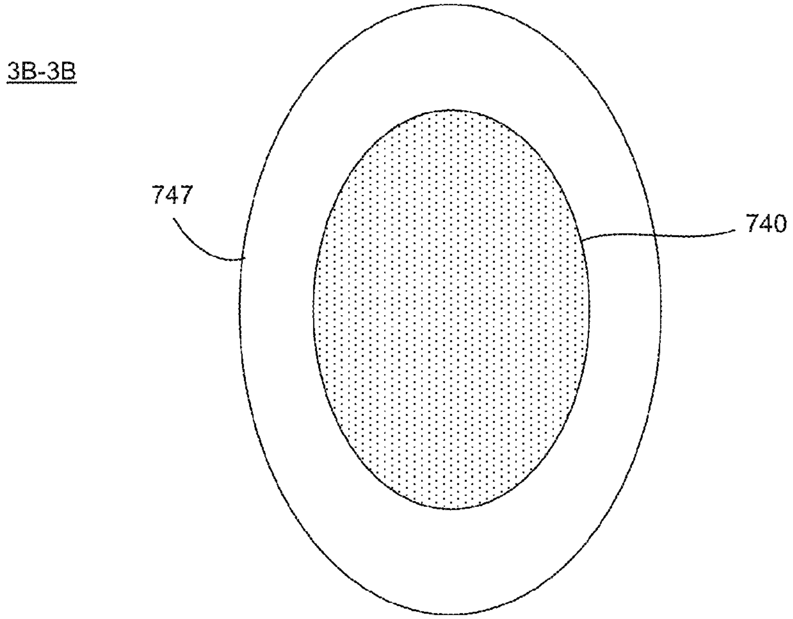
FIG. 7 is a diagram of an exemplary tube of the supply system of FIG. 3A taken along section 3B-3B.
Figure 8:
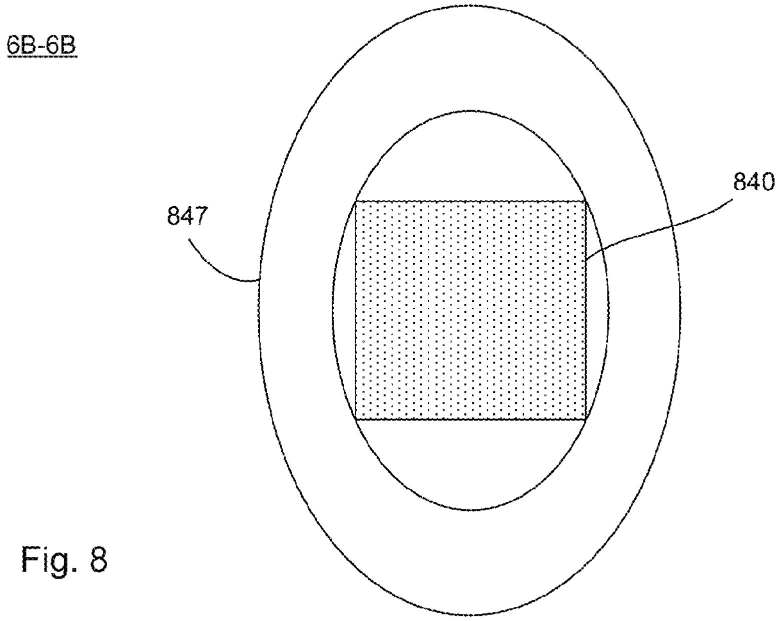
FIG. 8 is a diagram of an exemplary tube of the supply system of FIG. 6A taken along section 6B-6B.

The tube 247 of the supply system 245 could have any suitable cross sectional geometry; and the cross-sectional geometry of the tube 247 is not limited to the circular shape shown in FIGS. 3B and 6B. For example, referring also to FIGS. 7 and 8, the tube of the supply system 245 could have a cross section that is an oval geometry. In the example of FIG. 7, the cross-sectional shape of the filter 740 also has an oval geometry and in the example of FIG. 8, the cross-sectional shape of the filter 840 has a polygonal (for example, rectangular) shape.

Figure 9:
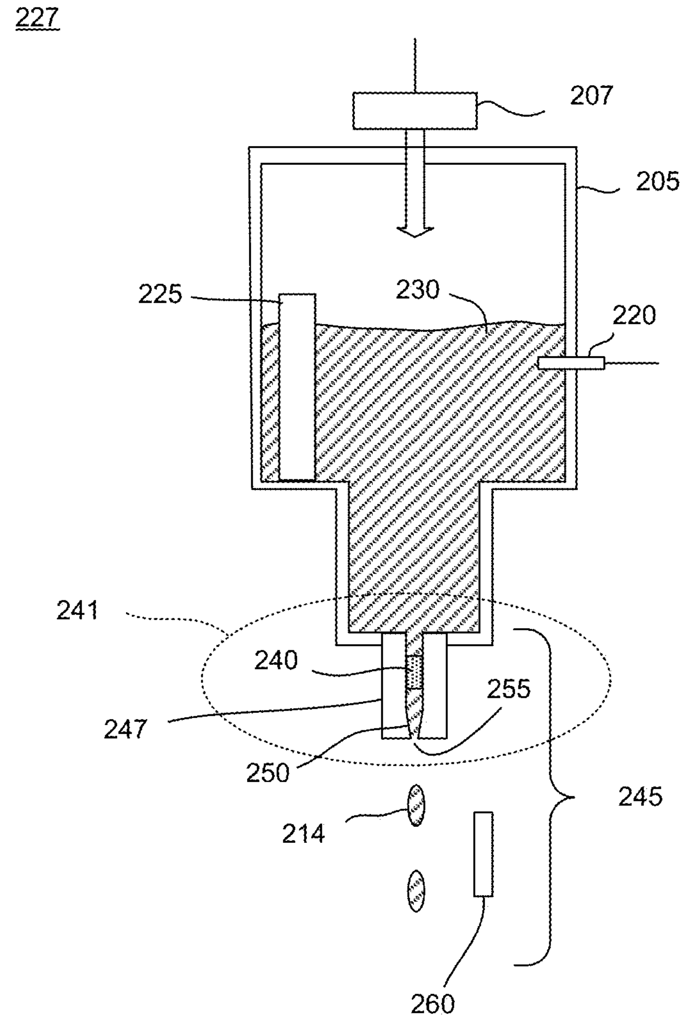
FIG. 9 is a schematic cross-sectional diagram of an exemplary target material supply apparatus of the light source of FIG. 1.

Referring to FIG. 9, in an exemplary implementation, a target material supply apparatus 227 includes only one chamber 205, which receives the bulk substance 225, which becomes a fluid target mixture 230 that is retained inside the chamber 205 until the supply system 245 requires additional target mixture 230. In other implementations, the target material supply apparatus 227 can include more than two chambers.

In another implementation in which a pre-made filter 240 is inserted into the tube 247 and then bonded or adhered to the interior surface of the tube 247, the pre-made filter 240 can be a micro-structured optical fiber having air holes or cores through which the target mixture 230 is passed. For example, the fiber could be a photonic crystal fiber or holey fiber that includes a hexagonal lattice of air holes in a silica fiber, with or without a solid or a hollow core at the center; an irregular lattice of air holes; or concentric rings of air gaps. Such a micro-structured optical fiber could be made of glass such as quartz or silica.

Other implementations are within the scope of the following claims.

What is claimed is:

1. An apparatus for supplying a target material to a target location, the apparatus comprising:
- a reservoir that holds a target mixture that includes the target material and non-target particles;
- a supply system that receives the target mixture from the reservoir and that supplies the target mixture to the target location, the supply system including comprising:
  - a capillary tube, and
  - a nozzle at an output of the capillary tube that defines an orifice through which the target mixture is passed; and
- a filter inside the capillary tube through which the target mixture is passed.

2. The apparatus of claim 1, wherein the filter is a sintered filter.

3. The apparatus of claim 1, wherein the filter and the tube are arranged so that the target mixture passes through the filter.

4. The apparatus of claim 3, wherein the filter includes pores through which the target material passes.

5. The apparatus of claim 4, wherein the size of the pores within the filter is determined by the size of the nozzle and orifice.

6. The apparatus of claim 5, wherein the size of the nozzle and orifice is determined by the size of the target material.

7. The apparatus of claim 3, wherein the filter pores are uniformly sized.

8. The apparatus of claim 3, wherein the filter pores are non-uniformly sized.

9. The apparatus of claim 1, further comprising a second filter that is upstream of the supply system.

10. The apparatus of claim 9, wherein the filter has a coarser porous structure than the second filter.

11. The apparatus of claim 9, wherein the filter has a finer porous structure than the second filter.

12. The apparatus of claim 9, wherein the second filter is a sintered filter.

13. The apparatus of claim 1, wherein one or more of the filter, the tube, and the nozzle are made of glass.

14. The apparatus of claim 13, wherein the glass is fused silica or fused quartz.

15. The apparatus of claim 1, wherein the filter is integrated with the tube.

16. The apparatus of claim 15, wherein the filter is bonded to the internal wall of the tube.

17. The apparatus of claim 1, wherein the filter is a porous fritted filter.

18. The apparatus of claim 1, wherein the filter is placed within the tube adjacent the nozzle.

19. The apparatus of claim 1, wherein the filter is made of a material that does not chemically react with the target mixture.

20. The apparatus of claim 1, wherein the filter is made of ceramic.

21. A method for supplying a target material to a target location, the method comprising:
- heating a bulk substance of a target mixture until the bulk substance becomes a fluid of the target mixture, the target mixture including target material and non-target particles;
- holding the target mixture fluid within a reservoir;
- passing the target mixture fluid through a nozzle capillary tube of a supply system;
- filtering at least some of the non-target particles from the target mixture fluid as the target mixture fluid passes through the supply system nozzle capillary tube; and
- supplying the filtered target mixture fluid to the target location including passing the filtered target mixture through an orifice of a nozzle defined at the end of the nozzle capillary tube.

22. An apparatus for supplying a target material to a target location, the apparatus comprising:
- a supply system that is configured to receive a target mixture from a reservoir and to supply the target mixture to a target location, the supply system including a capillary tube defining an internal passageway and a nozzle at an end of the capillary tube, the nozzle defining an orifice; and
- a filter inside of the internal passageway of the capillary tube and integrated with the capillary tube such that the target material passes through pores within the filter while traveling through the capillary tube.

23. An extreme ultraviolet light system comprising:
- an apparatus for supplying a target material to a target location, the apparatus comprising:
  - a reservoir that holds a target mixture that includes the target material and non-target particles;
  - a supply system that receives the target mixture from the reservoir and that supplies the target mixture to the target location, the supply system including a capillary tube and a nozzle at an output of the capillary tube that defines an orifice through which the target mixture is passed; and
  - a filter inside the capillary tube through which the target mixture is passed;
- a light source that supplies an amplified light beam; and
- a beam delivery system at the output of the light source for directing the amplified light beam along a beam path toward the target location to irradiate the supplied target material with the amplified light beam to thereby produce extreme ultraviolet light.

* * * * *